United States Patent [19]

Odeyale et al.

[11] Patent Number: 5,162,990
[45] Date of Patent: Nov. 10, 1992

[54] SYSTEM AND METHOD FOR QUANTIFYING MACROPHAGE PHAGOCYTOSIS BY COMPUTER IMAGE ANALYSIS

[75] Inventors: Charles O. Odeyale, Severn; Gregory R. Hook, Silver Spring, both of Md.

[73] Assignee: The United States of America as represented by the United States Navy, Washington, D.C.

[21] Appl. No.: 540,666

[22] Filed: Jun. 15, 1990

[51] Int. Cl.$^5$ .................. G06F 15/00; G06F 15/42
[52] U.S. Cl. ............................ 364/413.1; 364/922.2; 250/572
[58] Field of Search .................. 364/413.01–413.1; 250/572; 382/6

[56] References Cited

PUBLICATIONS

The IBAS Bag of Tricks, Jul. 1984 (4 pages).
J. Immunological Methods, 64, pp. 71–83 (1983) Elsevier.
J. Histochemistry and Cytochemistry, vol. 33, No. 6, pp. 551–556 (1985).
Methods in Enzymology, vol. 132, pp. 183–192, (1986).
Reviews of Infectious Diseases, vol. 10, No. 1, pp. 92–102, (Jan.–Feb., 1988).
Reviews of Infectious Diseases, vol. 11, No. 1, pp. 16–33, (Jan.–Feb., 1988).
Infection and Immunity, pp. 917–919, (Dec., 1986).
Eur. J. Clin. Microbiol., pp. 379–391, (Aug. 1985).

Primary Examiner—Emanuel S. Kemeny
Attorney, Agent, or Firm—A. David Spevack; William C. Garvert

[57] ABSTRACT

The present invention is embodied in a method and algorithm for rapidly quantifying phagocytic functions using computer image analysis (CIA) of video light microscopic images. The method and algorithm involve sequential acquisition of bright field or phase contrast and epi-fluorescence video microscopic images of respective field, addition of the images, decision making, object referencing, morphological feature extraction, arithmetic operations, and statistical analysis. This invention provides significantly faster phagocytic functions analysis than manual microscopic examination and more detailed quantitative morphological data than flow cytometry.

14 Claims, 5 Drawing Sheets

IMAGE ANALYSIS PROCEDURE

BLACK ON GREY-ORIGINAL VIDEO DIGITIZED IMAGE OF CELLS (25x, NA 0.45)

WHITE ON BLACK-CORRESPONDING ORIGINAL FLUORESCENT IMAGE OF MICROSPHERES FROM THE SAME FIELD AS (A).

BINARY CELL (LIGHT BLUE) AND FLUORESCENT MICROSPHERE (DARK BLUE) IMAGES ADDED TOGETHER

RANDOM COLORS ASSIGNED AND SIGNIFY EACH CELL INDIVIDUALLY ANALYZED

SYSTEM AND METHOD FOR QUANTIFYING MACROPHAGE PHAGOCYTOSIS BY COMPUTER IMAGE ANALYSIS

BACKGROUND OF THE INVENTION

1. Field of the Invention

This invention relates to a system and method for quantifying by computer image analysis relatively smaller enclosed objects within relatively larger objects. More particularly, this invention relates to a system and method for quantifying macrophage phagocytosis by computer image analysis, and to a method of utilizing the system and method of this invention to evaluate the pathophysiologic, and/or therapeutic effects of any agent by quantifying their endocytic functions and morphological effects.

2. Description of the Prior Art

Generally, phagocytosis is the most important defense mechanism in all phyla of the animal kingdom [van Oss, CJ. Methods of Enzymology,132,3, 1986]. It has an essential role in host defense mechanism against bacterial and/or viral infection(s) [Walters and Papadimitriou, 1978; van Oss, CJ. et al., Phagocytic Engulfment and Cell Adhesiveness, 1975], and the removal of foreign objects, intact red cells and/or red cells that have been fragmented, hemolyzed or are in the process of hemolysis. Increased susceptibility to infection has been reported [Bjorksten, B, and Quie, PG. Abnormalities of Circulating Phagocyte Function, p.181, 1977; Holmes, B. et al., J. Clin. Inv. 46, 1422, 1976] to be associated with defective phagocytic function. Since the phenomenon of phagocytosis was first reported by Haeckel in 1862, several methods for quantitative study of phagocytosis, which can be divided into direct and indirect methods, have been reported, and recently reviewed [van Oss, CJ. Methods of Enzymology, 132,3 1986]. They include microscopic methods, isotopic labeling methods, extraction methods, unphagocytized test particles removal, and measurement of glycolysis, degranulation and respiration activity burst. Current single cell methods for quantifying phagocytosis are either direct microscopic examination [Dunn, PA. et al., J. Immunol. Methods, 64, 71 1983] or by flow cytometric analysis [Absolom, DR, Methods of Enzymology, 132, 95 1986; Bjerknes, B. et al., Rev. Infect. Dis., 11, 16, 1989; Verhoef, J. and Waldvogel, Eur. J. Clin. Microbiol., 4, 379 1985]. Light microscopic examination and manual counting of particles in individual cells is the most common method of quantifying phagocytosis, but only a few cells can be analyzed and no quantitative morphometric data is obtained. Flow cytometry can quantify phagocytosis of many cells in suspension [Dunn, PA and Tyrer, HW, J. Lab. Clin. Med., 98, 374 1981; Steinkamp, JA et al., Science, 215, 64 1982], but cannot provide detailed morphometric data. Besides, the process of most of these methods is time consuming, some are relatively unsafe, and the microscopic methods, in particular, in addition to time consuming and labor intensive, is subjective, only approximate and statistically weak. The inadequacy of these methods has been emphasized in several papers.

Also, computerized systems for quantifying of morphologic and physiologic parameters related to phagocytosis, e.g. intracellular enzymes and ions contents, cell migration, cell surface areas, etc., have recently been reported (Goldstein, E. et al., Reviews Infect. Dis., 10, 92 1988; Askey, DB and Herman, IM, Comput. Biomed. Res., 21, 6, 551 1988). However, intracellular enzymes and ions contents are only indirect methods for the determination of phagocytic function(s). Although cell migration and surface areas may be indicative of the occurrence of infection, they do not provide information needed to evaluate the physiologic, and/or therapeutic effects of agents on phagocytic functions. Furthermore, cytospectrophotometric and image analysis systems which aid non-cumbersome measurement of cellular enzymatic activities and/or functions [Goldstein, E. et al., Reviews Infect. Dis., 10, 92, 1988; Black, CM. et al., Infect. & Immunity, 54, 917, 1986; Donovan, RM and Goldstein, EA, J. Histochem. Cytochem., 33, 551, 1985; Black, CM. et al., J. Infect. Dis., 148, 117, 1983; Goldstein, E. et al., J. Infect Dis., 138, 299, 1978] and quantify morphologic parameters [Hoshino, K, J. Histochem. Cytochem., 31, 1A Suppl, 1983; Erhardt, R. et al., Anal. Quant. Cyto. Histol., 2, 25, 1980] have been produced by the application of computer (first essentially through software engineering, now being improved by both hardware and software developments) and electronics technologies. Although the applications of these systems permit fast and accurate analyses of large population in such a way which would have been impossible using non-computerized microscopic methods, they can not be used for direct quantitative analysis of phagocytic functions.

The lack of computerized quantifying of phagocytic functions has thus far impeded phagocytosis studies involving large number of cells leading to accurate statistical analysis.

The following are the references referred to above by the name of of the author and below by reference number. These references provide further background information to the invention or the description of specific techniques which are incorporated in this application by reference to the extent needed.

SUMMARY OF THE INVENTION

Accordingly, it is an object of this invention to provide an accurate and rapid method for computer assisted quantitative analysis of enclosed objects in a larger object whereby the later is alone or with others in an image field.

A further objective of the invention is to provide an accurate and rapid computer assisted quantitative phagocytosis method that will enhance immunological and pathophysiological lines of research by screening for and detecting substance phagocytosability; the efficacy of immunization with bacterial extracts; resistance of and/or to bacteria; and wound healing.

Yet, another objective of this invention is to provide a method that would certainly lead to marked improvement in clinical management of sepsis and/or septic shock adverse effects and further scientific understanding of the conditions in general.

An additional object of this invention is a method and algorithm for accurate and rapid quantitative assessment of phagocytic functions, which include but are not limited to avidity index, phagocytic index, phagocytic activity index, rate, and capacity.

These and additional objects of the invention are accomplished by a system for quantifying objects having at least an imaging means for forming at least two types of images; a sample mount for mounting a sample containing target cells in said imaging means wherein the target is a relatively large object capable of engulfing smaller enclosed objects; a first light source mounted on said imaging means for projecting a first type of light on said sample and forming a contrast image as a first image; a second light source mounted on said imaging means for projecting a second type of light on said sample and forming a second image having a different grey value than said first image; recording means for recording said first and second images; digitizing means for digitizing said first and second images to form digitized first and second images; filtering means to filter said first digitized image to form a filtered image; segmenting means to convert the filtered image and the second digitized image to form first and second binary images; means for inverting said second binary image to form an inverted binary image; computing means for adding the first binary image and the inverted binary image to form a composite image and determining the number of engulfed objects per target cell using the following formula $GV = ((0*M) + (255*C))/AR$ wherein GV is the grey value, AR is the total area of both cell and microspheres, M is the weighted average of the microsphere area and C is the cell area.

The invention also includes a method of quantifying objects comprising: providing a sample containing target cells wherein the target cell is a relatively large object capable of engulfing smaller enclosed objects and smaller potentially enclosed objects; viewing the sample through an imaging means capable of forming at least two types of images; projecting a type of light from a first light source on the sample to form a contrast image as a first image; projecting a second type of light on the sample from a second light source to form a second image having a different grey value than said first image; recording the first and second images; digitizing the first and second images to form digitized first and second images; filtering the first digitized image to form a filtered image; segmenting the filtered image and the second digitized image to form first and second binary images; inverting said second binary image to form an inverted binary image; adding the first binary image and the inverted binary image to form a composite image; and determining the number of engulfed objects per target cell in the composite image using the following formula $GV = ((0*M) + (255*C))/AR$ wherein GV is the grey value, AR is the total area of both cell and microspheres, M is the weighted average of the microsphere area and C is the cell area.

The invention also includes a method of detecting endocytosis related disease and disfunction or foreign substances in the system.

BRIEF DESCRIPTION OF THE DRAWINGS

A more complete appreciation of the invention will be readily obtained by reference to the following Detailed Description and the accompanying drawings in which like numerals in different figures represent the same structures or elements. The representations in each of the figures is diagrammatic and no attempt is made to indicate actual scales or precise ratios. Proportional relationships are shown as approximations.

(A) Original video digitized image of cells (25x, NA 0.45);

(B) corresponding original fluorescent image of microspheres from the same field as (A);

(C) Binary cell (light blue) and fluorescent microsphere (dark blue) images added together;

(D) Processed field from which background microspheres have been eliminated before measurement; random colors assigned and signify each cell individually analyzed.

Figure 4:
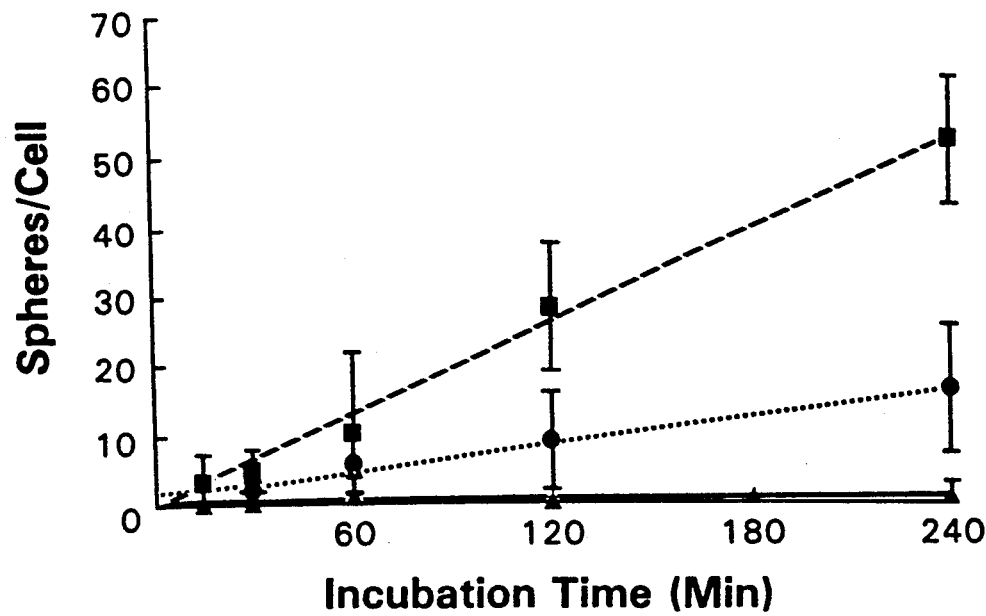

FIG. 4 is a graph showing a comparison of the time-course of phagocytosis with respect to increase in the concentration of microspheres and incubation temperature.

Figure 5:
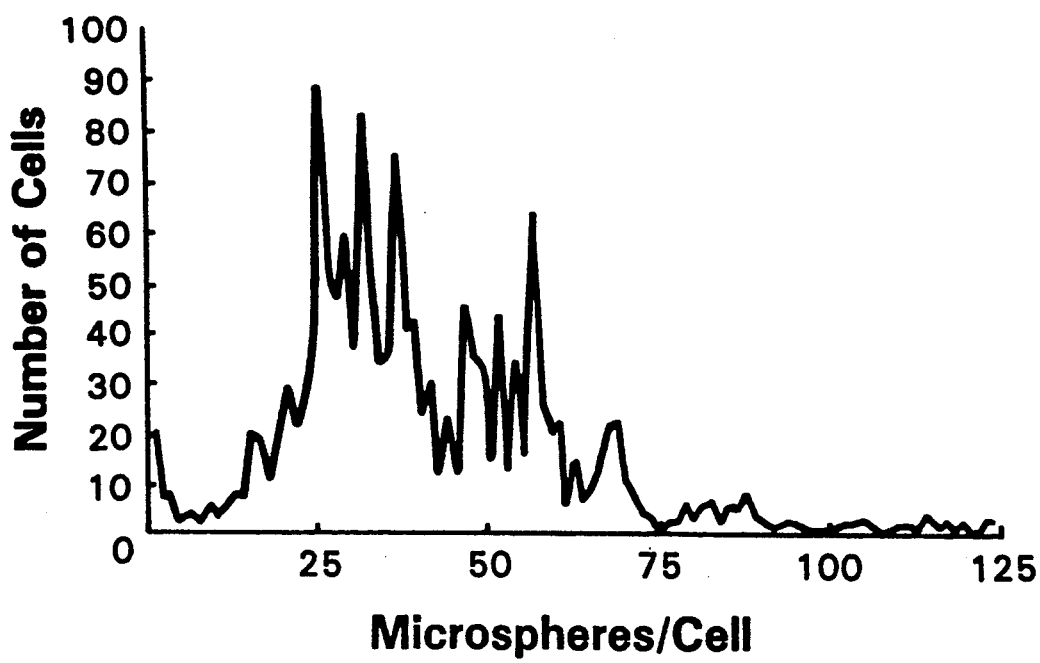

FIG. 5 is a histogram of microspheres per cell indicating possible bimodal distribution with peaks centered around 25 and 55 microspheres per cell.

Figure 6:
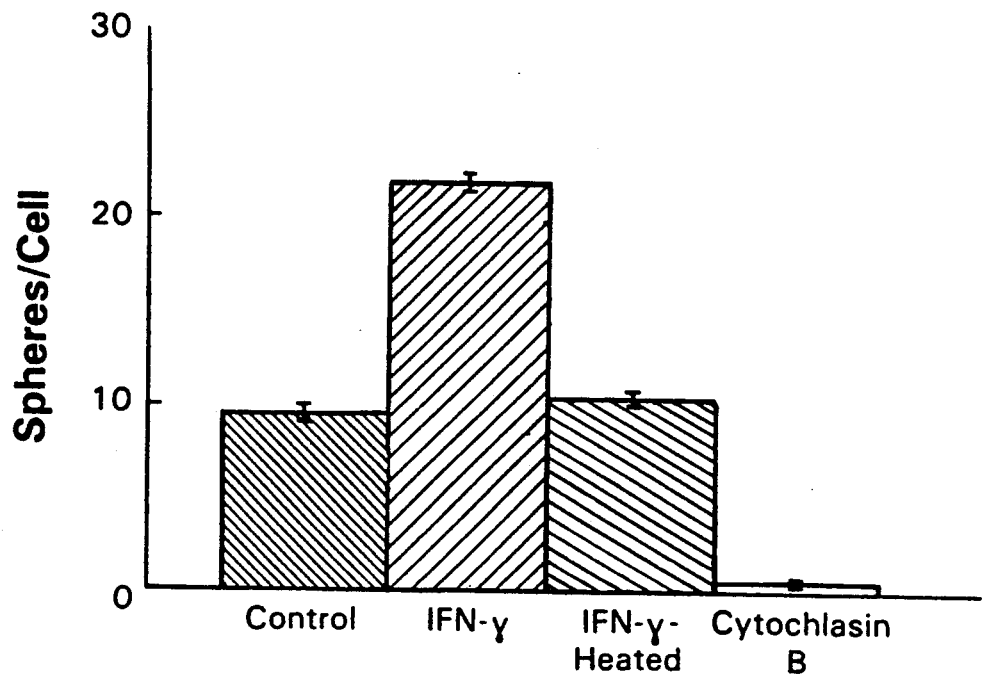

FIG. 6 is a graph of the phagocytic response of macrophages to heated and unheated INF, and cytochalasin B.

Figure 7:
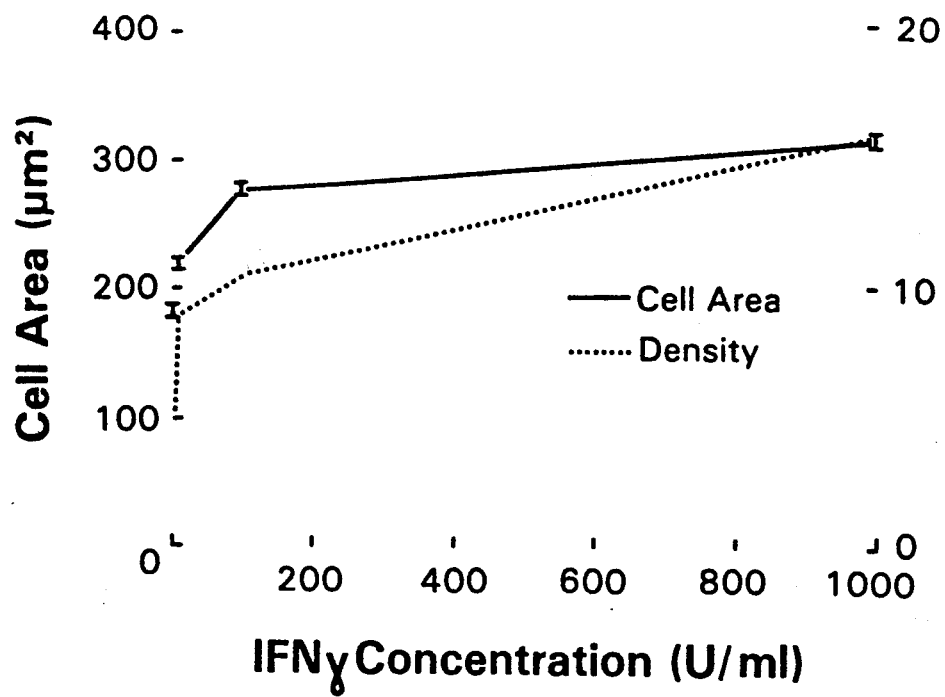

FIG. 7 is a graph showing the morphohetric response of macrophages to increasing concentration of INF showed cell area ( . . . ) and density ( . . . ) increased with INF concentration.

Figure 8:
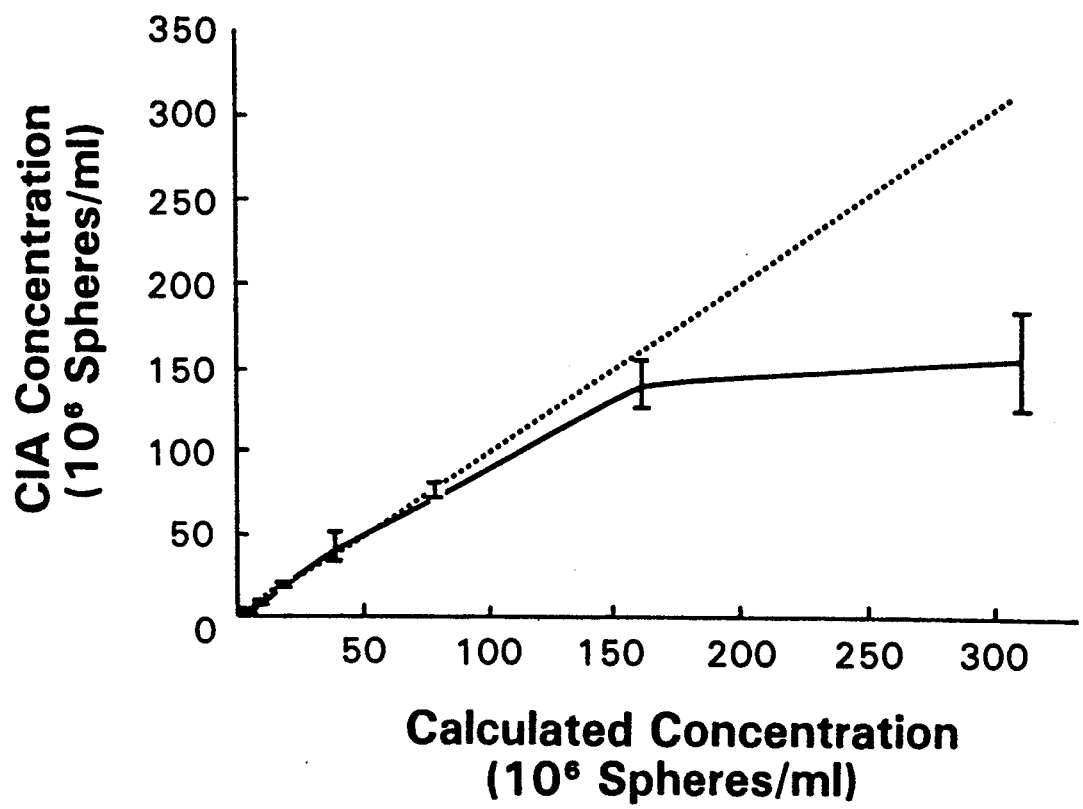

FIG. 8 is a comparison of microsphere concentration determined by CIA (-) and theoretical calculation ( . . . ).

DETAILED DESCRIPTION

The present invention is based on the concept that the mean grey value of an object and its enclosed relatively smaller objects is proportional to the object area occupied by the smaller objects. More particularly, the invention is predicated upon knowing that the number of object in a mass, whose total projected area is known, can be accurately and rapidly calculated by dividing the total projected area by the area of a single object composing the mass. Although the invention is illustrated with counting microscopic materials, the invention is equally applicable to any similar counting problem and, by way of example, can be used in astronomy for counting individual stars in a star cluster or distant galaxy.

Generally, the method of this invention rapidly quantifies phagocytosis using computer image analysis (CIA) of video light microscopic images. Ingestion of fluorescent microspheres by peritoneal murine macrophages is used to model phagocytosis. The grey levels of digital phase contrast and fluorescent microscopic images are used to quantify the number of microspheres per cell. The method is semi-automatic, analyzes approximately $2 \times 10^3$ cells/hour and simultaneously measures phagocytosis (microspheres/cell), cell area, and density (number of cells/mm$^2$). For countable microspheres in cells, CIA obtains the same microspheres/cell average as manual microscopic counting and an analytical precision of 5%, it is also able to easily and rapidly quantify samples that are difficult or impossible for manual microscopic counting. As expected, CIA finds that the number of microspheres/cell linearly increases with increasing macrophage-microsphere coculture time or increasing microsphere concentration until macrophages became saturated. CIA finds increased phagocytosis by interferon-gamma treated cells and suppressed phagocytosis by cytochalasin B or 4° C. treated cells relative to controls, which demonstrates that CIA can resolve biological changes in macrophage phagocytosis. Also, CIA provides quantitative data on macrophage morphometry and density and finds an increase in the cell area and density of INF treated macrophages. CIA provides significantly more phagocytic, morphometric and density data than conventional manual microscopic counting methods or flow cytometric methods.

The method and algorithm of the preferred embodiment include sequential acquisition of bright field or phase contrast and epi-fluorescence video microscopic images of respective field, addition of the images, decision making, object referencing, morphological feature extraction, arithmetic operations, and statistical analysis. The invention further contemplates a method and algorithm by which cell sub-classes can be determined based on phagocytosis.

Figure 1:
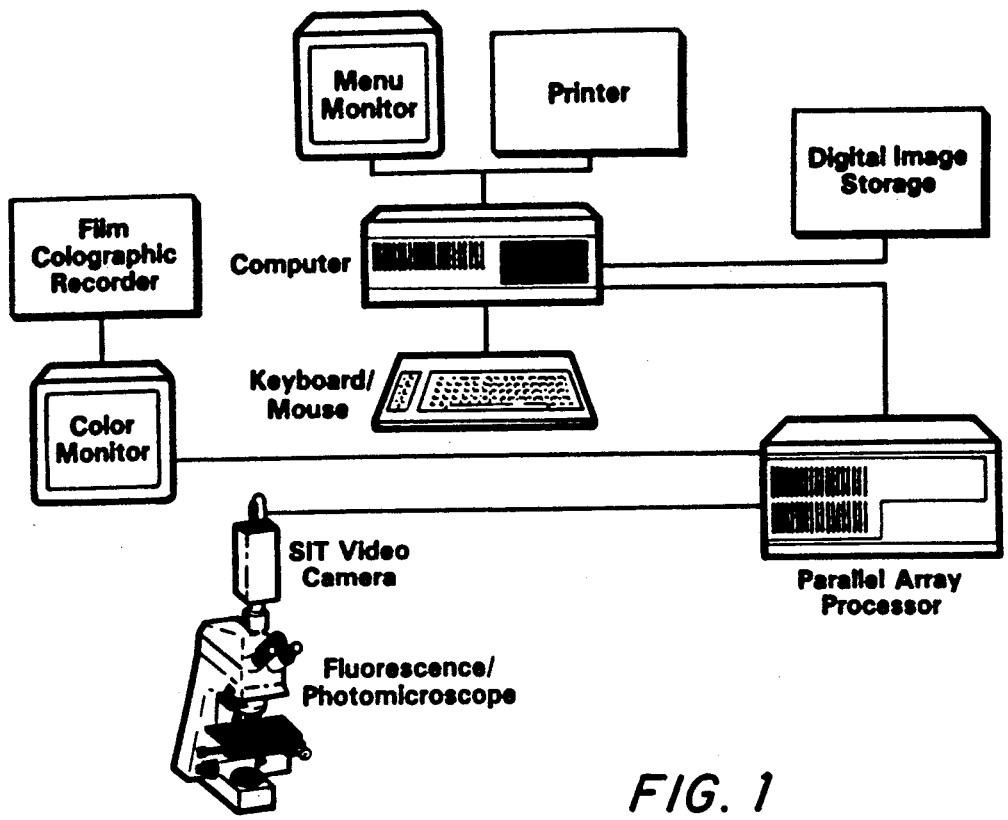
FIG. 1 is a flow diagram of the image processing system used for macrophage phagocytosis.

Referring to the drawings where in FIG. 1, the light microscope and computer image analysis system are diagramed using a SIT video camera as the image forming system for on-line analysis. In one embodiment, the computer image analysis system is a Kontron-Zeiss SEM-IPS (Carl Zeiss, Inc., Thornwood, NY) attached to an upright light microscope (Photomicroscope II, Carl Zeiss, Inc., Thornwood, NY) equipped with phase contrast optics, mercury arc epi-illumination (50 watts) and fluorescence bandpass filters (458 nm excitation, 540 nm emission center wavelength). A low light silicon intensified target video camera (SIT 66, DAGE-MTI Inc., Michigan City, IN) makes video images of the cells and microspheres. The on-line video images are digitized via a parallel array processor under interactive control of a Zilog Z8OA (4MHz)-based host computer with CP/M operating system. Digitized images are stored in one of the seven $512 \times 512 \times 8$ bit volatile memory planes of the SEM-IPS during analysis. The number of memory planes is limited by the number of memory chips installed. The images can be stored permanently on 10 megabyte removable IOMEGA disks.

A commercially available software system, IBAS, release 4.4 (Carl Zeiss, Inc., Thornwood, NY) is used to analyze the images. The IBAS is a menu driven system having a large selection of image acquisition, enhancement, analysis and display subroutines. The IBAS may be used to create a macro program consisting of both IBAS and user-written subroutines that may be automatically executed with IBAS' subroutines if the system is so instructed. The program is prepared using standard techniques to meet the parameters stated. Although this program currently run within the IBAS environment, the basic principle of the method can be adapted and used on other image analysis systems.

Figure 2:
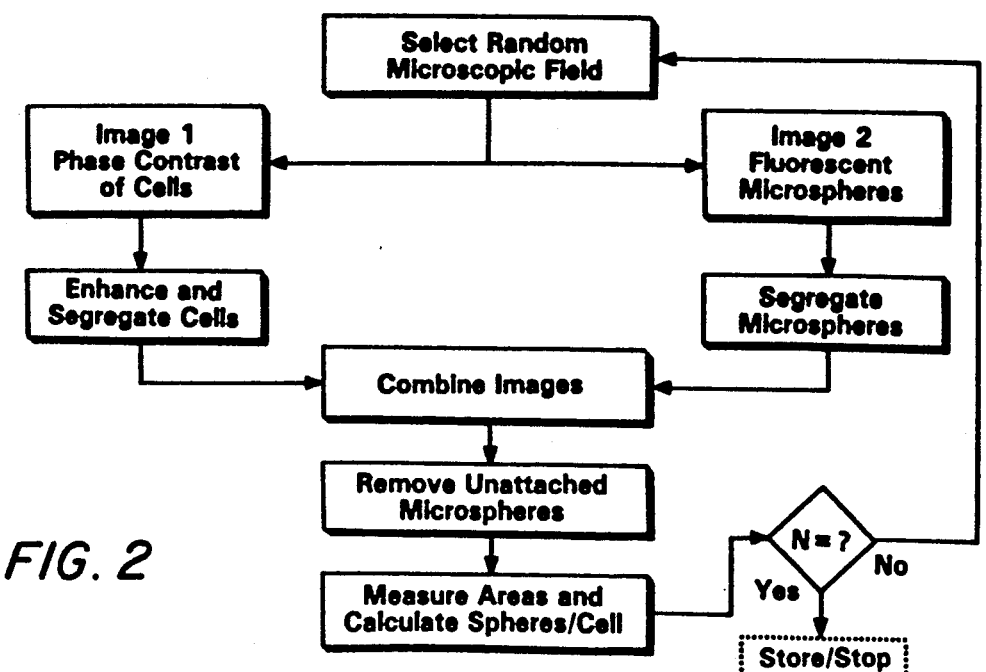
FIG. 2 is the schematic flow diagram of the image analysis procedure.
Figure 3A:
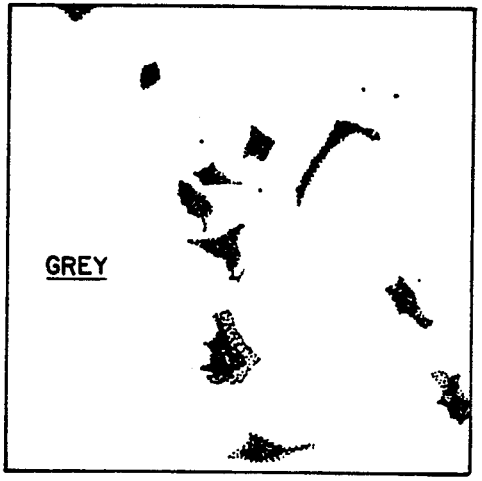
FIGS. 3A to 3D are the sequence for measuring the number of microspheres per cell using CIA.
Figure 3B:
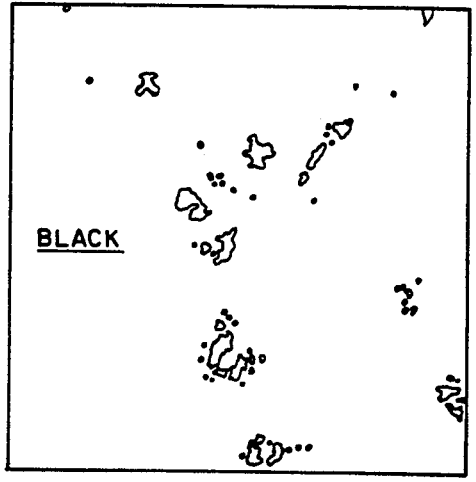
Figure 3C:
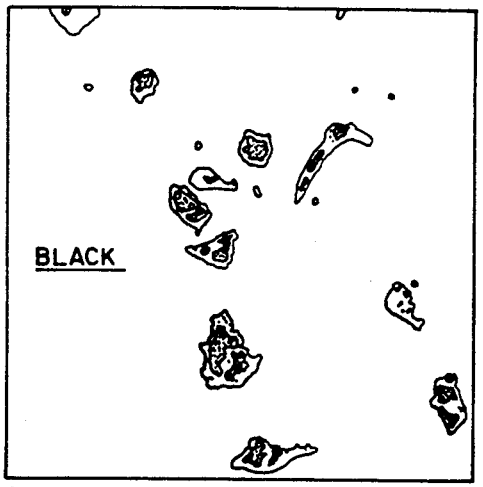
Figure 3D:
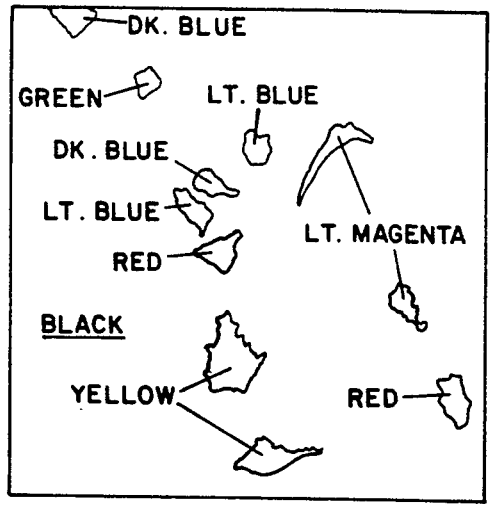

FIG. 2 is the schematic flow diagram of the image analysis procedure. The user selects random microscopic fields from which phase contrast and corresponding fluorescent images are taken separately, segregated and added to measure cell areas and calculate the number of microspheres per cell. In the procedure, non-overlapping random fields of cells are examined using a phase contrast microscope with a $25 \times$, NA 0.45, objective lens. This magnification maximizes the number of cells observed while providing sufficient magnification and resolution of the microspheres and cells. After optimal adjustment of the video camera, phase contrast and epi-fluorescence video microscopic images of each field are sequentially recorded. A video phase contrast image of the cells is obtained after adjusting the light and video camera to maximize the contrast. The video image is digitized, frame-averaged (three times) and stored in a computer image plane (random access memory). Without changing the field, a fluorescent image of the microspheres is made by turning off the phase contrast illumination and turning on the epi-fluorescent illumination. The fluorescent image is digitized, frame averaged and stored in a separate image plane.

To remove artifacts in the image caused by dirt in the optical system, a defocused background image frame is subtracted from the original image frame. This is done by defocusing the microscope, frame-averaging, digitizing, and storing the background phase contrast image frame. To make the cells completely dark, the resulting image is scaled by making grey values from 0 to 120 black (0) and 121 to 255 white (255), then enhanced by a ranked median filter (kernel size $5 \times 5$, rank 13). The ranked median filter is a group-like process operating on a $5 \times 5$ pixel neighborhood. The center-pixel grey value output of the filter is the median value of the twenty-five pixel brightness values. The median value of a neighborhood is determined by placing the twenty-five brightness values into ascending numerical order and selecting the center value to replace the original grey value.

The cells within the enhanced phase contrast field are selected by grey level discrimination and transformed into a binary image. The first field discrimination is done interactively by the operator; the rest of the fields are discriminated automatically using the selected grey value window to produce consistent grey value dependent object areas. The fidelity of the discrimination is evaluated by overlaying contour maps of the binary images on the original phase contrast images. The fluorescent microsphere images are also discriminated from the background and inverted to black so that the microspheres could be differentiated from the cell. The cell and fluorescent binary images are added and stored. The cells and microspheres have grey values of 255 (white) and 0 (black), respectively, in the composite image (see FIG. 3). The number of microspheres in each cell is as calculated from the composite binary image. Microspheres not associated with cells are eliminated from the analysis by size "thresholding."

The number of microspheres per cell is calculated by dividing the total areas of the black microspheres and white cells, the mean grey value (GV) is computed and is proportional to the cell area occupied by microspheres. The GV, which is the weighted average of the microsphere area (M) and the cell area (C), is given by the formula:

$$GV = ((0*M) + (255*C))/AR$$

where AR is the total area of both cells and microspheres. The proportion of each cell's area occupied by microspheres (A) is:

$$A = (1 - (GV/255))$$

and total microsphere area of each cell (MA) is:

$$MA = A*AR$$

The number of microspheres per cell (MC) is:

$$MC = MA/SM$$

where SM is the area of a single microsphere. Since only whole microspheres are possible, the quotient is rounded off to the nearest whole integer.

Having described the invention, the following examples are given to illustrate specific applications of the invention including the best mode now known to perform the invention. These specific examples are not intended to limit the scope of the invention described in this application.

Macrophage Harvest and Phagocytosis

Standard peritoneal lavage and culture techniques were used to obtain murine peritoneal exudate cells and macrophage enriched cell cultures. Ten to twelve-week-old female BALB/CJ mice (Jackson Laboratories, Bar Harbor, ME) were sacrificed by cervical dislocation by an individual trained in such euthanasia. Animals were placed in a supine position, the abdominal area wetted with 70% alcohol, and the abdominal skin cut and retracted. The animals were injected intraperitoneally with 4 ml cold Hanks' Balanced Salt Solution (HBSS, GIBCO Laboratories, Grand Island, N.Y.), gently rotated and shaken (1 min), incised below the sternum and peritoneal exudate fluid removed using a sterile Pasteur pipet. The exudate cells were pooled into 50 ml centrifuge tubes (Labcon, San Rafael, CA) and washed twice in cold HBSS by centrifugation at $200 \times g$ for 10 min. at 5° C. (CRU-50, Damon/IEC Division, Needham Hts, MA). The pellet was reconstituted in RPMI 1640 growth media (Flow Laboratories, McLean, VA) containing 10% fetal calf serum (FCS, lot 27N1072, Gibco Laboratories, Grand Island, NY), 2% HEPES, 0.1% gentamicin, and 1% glutamine to a concentration of approximately $2.5 \times 10^6$ cells/ml. Peritoneal exudate cells, plated at $2.5 \times 10^6$ cells/dish in 3 ml of media in tissue culture dishes ($60 \times 15$ mm, Costar, Cambridge, MA), were incubated in a 5% $CO_2$ atmosphere at 37° C. overnight (Model 3185, Forma Scientific, Marieta, OH). Non-adherent cells were removed from the cultures by briskly rinsing each dish three times with 3 ml/wash of cold HBSS. To use non-adherent cells, poly-L-lysine has been used to adhere cells to glass slides.

To determine if CIA could resolve biological changes in macrophage phagocytic function, macrophages were cultured with agents known to affect phagocytosis. To inhibit phagocytosis, microspheres and macrophages were either co-cultured at 4° C. or macrophages were pretreated with cytochalasin B ($4 \times 10^{-5}$M, Sigma, St. Louis, MO) for 1 hour before and during microsphere co-culture. To enhance phagocytosis, macrophages were cultured with recombinant murine interferon-gamma (INF, Genzyme, Boston, MA) at various concentrations (10, 100 and 1000 U/ml) 24 hrs before microsphere co-culture. As a control for possible lipopolysaccharide (LPS) contamination of INF, an aliquot of INF (1000 U/ml) was heated (100° C., 1 hr) to denature it (but not LPS) before adding the INF to the cultures.

Macrophage culture media was decanted off and fluorescent microspheres of various known concentrations in growth media were added to the cultures (3 ml/dish). Concentrations of $2 \times 10^8$ and $4 \times 10^8$ microspheres/ml were used to give cell-to-microspheres ratios of 1:80 and 1:160, respectively. The macrophage and microsphere co-cultures were incubated in 5% $CO_2$ at 37° C. for various lengths of time. After incubation, the cultures were jet-stream washed ($3\times$, cold HBSS), fixed (10 min, cold 2% glutaraldehyde, 2 mM $CaCl_2$ in 0.1M cacodylate buffer pH 7.2), washed ($3\times$, 0.1M cacodylate buffer), stained (2 min, Wright-Giemsa quick stain, Curtain Matheson Scientific, Inc. Houston, TX), decanted, and dried before analysis. To aid the segregation of the objects from the background, the staining procedure should be repeated if a thin blue film is not visible to the naked eyes after washing off the dye.

Microspheres

Uniformly sized fluorescent carboxylate microspheres (1 μm diameter 1.5% standard deviation, yellow-green fluorescence, 458 nm maximum excitation, 540 nm maximum emission, Catalog #15702, Polysciences, Warrington, Pa.) were used for all studies. A stock microsphere suspension (200 μl) was washed in HBSS by centrifugation ($11950 \times g$, 15 min, 5° C., Sorvall RC-5B, DuPont Instruments, Newtown, CT) and resuspended in growth media (40 ml). To determine the concentration of microspheres, an aliquot of the suspension was diluted in distilled water and analyzed by CIA. Three drops (1 μl each) of the appropriate dilution were placed on a clean glass microscope slide, dried and counted using the microscope and CIA system. Microspheres in the entire area of the drop were counted and the number of microspheres per ml was calculated from the result based on the dilution. The theoretical microsphere concentration (TC) was calculated and compared to CIA analysis using the following:

$$TC = (6W*10^{12})/(p*\pi*d^3)$$

where W is the concentration of polymer (0.025 g/ml), p is density of polymer (1.05 gm/ml), and d is the diameter of the microspheres (1 μm). Accuracy and precision was improved by calibrating the number of microspheres in a field obtained by CIA to the number obtained by manual methods before beginning analysis of an unknown.

Results and Discussion

No significant difference was found in the mean number of microspheres per cell determined by CIA and manual microscopic counting (p=0.144, Student's t test, N=69, see Table 1).

TABLE 1

A Comparison Between the Mean Number of Microspheres per Cell Determined by CIA and Manual Microscopic Counting[a]

| No. field | No. of cells | Manual count (spheres/cell) | CIA (spheres/cell) | P[b] |
|---|---|---|---|---|
| 6 | 69 | 17.3 +/− 11.4 | 16.3 +/− 10.9 | 0.144 |

[a]Values are given as mean +/− SD. The cells and microspheres were co-cultured for 1 hr. at a cell-to-microsphere ratio of 1:160.
[b]No significant difference by paired Student's t test.

The results of repetitive analyses of one field by three operators are shown in Table 2.

TABLE 2

Variability Among and Within Operators Using CIA to Analyze One Field Three Times[a]

| Operators | Analyses | | | CV (%)[b] |
|---|---|---|---|---|
| | 1 | 2 | 3 | |
| 1 | 14.0 +/− 12 | 13.8 +/− 12 | 14.0 +/− 12 | .6 |
| 2 | 15.0 +/− 11 | 15.1 +/− 13 | 13.4 +/− 11 | 5.0 |
| 3 | 16.5 +/− 14 | 13.0 +/− 11 | 14.3 +/− 12 | 10.0 |

TABLE 2-continued

Variability Among and Within Operators Using CIA to Analyze One Field Three Times[a]

| Opera- | Analyses | | | |
| tors | 1 | 2 | 3 | CV (%)[b] |
| --- | --- | --- | --- | --- |
| CV[c] | 6.7% | 6.0% | 2.6% | |

[a]Values are given as mean +/− SD. N = 8 cells.
[b]Coefficient of variation among analyses for a given operator. Operator 1 was trained whereas operators 2 and 3 were naive. The grand mean CV among analyses equals 5.2%.
[c]Coefficient of variation among operators. The grand mean CV among operators equals 5.1%.

The difference in CIA determined counts between and within operators is not significant, (P. 0.94, One-Way Analysis of Variance, N=24). FIG. 4 is a comparison of the time-course of phagocytosis with respect to increase in the concentration of microspheres and incubation temperature. With increasing incubation time and 37° C., the number of microspheres per cell increased for 1:80 ( . . . ) and 1:160 ( . . . ) cell-to-microsphere ratios. No phagocytosis occurred for the assay performed at 4° C. The display represents the mean +/− one standard deviation, N=1500 cells/point. FIG. 4 shows that the number of microspheres per cell linearly increased with increasing microsphere-cell co-culture time ($r^2=0.98$) and the number of microspheres per cell was greater for higher microsphere-to-cell ratios at a given co-culture time. Phagocytosis was completely suppressed by co-culturing the microspheres and cells at 4° C. We conclude that CIA can produce accurate data on phagocytosis with reasonable precision.

CIA may be particularly useful for determining macrophage sub-classes based on phagocytosis because CIA can rapidly analyze many cells. FIG. 5 is a typical histogram of the number of microspheres per cell indicating possible bimodal distribution with peaks centered around 25 and 55 microspheres per cell. The cells and microspheres were co-cultured for 2 hr. at a cell-to-microsphere ratio of 1:160. The data was obtained from analysis of 1500 cells in approximately 45 minutes. The histogram suggests there is a possible bimodal distribution in the number of microspheres per cell in the population. Because of the inherent functional heterogeneity reported for phagocytic cells (Cehn, P & Lehrer, RI, Blood 64, 147, 1984; Grallin, JI, Blood 63, 977, 1984; Krause, PJ, et. al., Blood 68, 200, 1986; Walker, WS, Immunology of the Macrophage, p. 91, 1976), analysis of a large number of cells is essential to resolve macrophage sub-classes since macrophage phagocytosis is highly variable. Further, CIA has the potential to measure three other phagocytic parameters that should allow more detailed analyses of macrophage sub-classes. From the number of microspheres per cell and the number of cells analyzed, other important phagocytic parameters, the percent phagocytic cells (phagocytic activity index), the number of microspheres phagocytized per phagocytic cell (avidity index), and the total number of microspheres phagocytized (phagocytic capacity), can be calculated. These additional phagocytic parameters are important for determining macrophage sub-classes. A major application of CIA will be screening for the effects of agents on cells that are able to engulf any object. FIG. 6 is the phagocytic response of macrophages to heated and unheated INF, and cytochalasin B. IFN increased phagocytosis and cytochalasin B decreased phagocytosis relative to controls ($p<0.01$, Student's t test, N=1,500 cells/group).

Heated gamma-interferon had no effect relative to control. The display represents the mean +/− one standard error of the mean, N=1500 for each point. FIG. 6 shows the stimulating or inhibitory effects of INF or cytochalasin B, respectively, on macrophage phagocytosis. The number of microspheres per cell for INF treated cells was significantly greater than control cells ($p<0.01$, Student's t test, N=1,500 cells/group) whereas heat inactivated-INF had no effect. IFN is a known macrophage activator (Roberts, WK. & Vasil, A. J. Interferon Res., 2, 519, 1982). Significant suppression of phagocytic function was found for cytochalasin B, a known phagocytic function inhibitor (Axline, SG & Reaven, EP Cell Bioll., 62, 647, 1974) ($p<0.01$, Student's t test, N=1,500 cells/group). Previously, CIA found enhanced macrophage phagocytosis of interleukin-4 (IL-4) treated cultures, which was dose and time dependent (Hook, GR et. al., Am. Soc. Cell Biol., 107, 6, #3964, 1989). The IL-4 enhancement results found by CIA are in agreement with those reported using conventional phagocytosis methods (Wirth, JJ, et. al., Immunology 66, 296, 1989). Therefore, CIA will be useful for screening the effects of chemicals such as cytokines or bacterial virulence factors on phagocytosis, the development of anti-microbial agents, and pathogenic model systems.

In addition to analyses of phagocytosis, CIA provides morphometric and cell density measurements. FIG. 7 is the morphohetric response of macrophages to increasing concentration of INF showed cell area ( . . . ) and density ( . . . ) increased with INF concentration. Increased cell area is due to activation by INF. The display represents the mean +/− one standard error of the means, N=1500 for each point. As shown in FIG. 7, INF had a pronounced effect on macrophage cell area and density. Other morphometric parameters, such as perimeter and shape factor ($perimeter^2/area$), can be obtained for more detailed analyses.

To achieve precise and consistent results, uniformly stained cells and relatively few non-phagocytozed (background) microspheres were required. The sample preparation described routinely achieved these critical conditions. Non-clustered, well stained cells and few non-phagocytosed microspheres, made automatic segregation easy and fast (approximately $2 \times 10^3$ cells/hour).

Although CIA has many advantages, there are also several inherent limitations some of which are the result of the computer algorithm. For example, the CIA measured concentration of the microspheres/ml departed significantly from the theoretical concentrations of the same sample (FIG. 8). FIG. 8 is a comparison of microsphere concentration determined by CIA (-) and theoretical calculation ( . . . ). A linear relationship (r}0.98) up to $1 \times 10$ microspheres/ml was found. CIA significantly underestimated the microsphere concentrations when the microsphere concentration exceeded this value. The reason CIA under-estimated the high microsphere concentrations is there are many microspheres that overlay each other and are not counted. The overlapping of microspheres was not a problem in macrophage analysis. These results showed a linear relationship ($r^2$: 0.98) up to $1 \times 10^8$ microspheres/ml, but CIA made a significant underestimation of higher concentrations. The reason for this is that many microspheres overlay each other in the higher concentrations and CIA determines the number of microspheres based on the projected area that means overlaying microspheres are counted as one microsphere. However, this is not a significant problem for macrophage phagocytosis measurements if the microspheres per cell are not excessively large. As shown in FIG. 4, the linear response between microspheres per cell and macrophage-microsphere co-culture time indicates that under the conditions used, microsphere pileup in microphages did not have a significant effect on the analysis.

A biological limitation of the analysis is that the carboxylated microspheres used have entirely different surface properties from bacteria. The use of antibody coated fluorescent microspheres instead of uncoated microspheres will avoid the limitation. In addition, bacterial hydrophilicity causes resistance to ingestion and/or digestion (van Oss, CJ, et al., Phagocytic Engulfment and Cell Adhesiveness, p. 61, 1975; van Oss, CJ, Methods in Enzymology, 132,3, 1986). Thus, varying the surface hydrophilicity of the microspheres can be used to model resistance to phagocytosis. Bacterial phagocytosis using fluorescent bacteria instead of microspheres in another embodiment. Because bacteria are significantly smaller than the microspheres (1 μm), high magnification will be required resulting in a greatly reduce the rate of analysis. The asymmetric shape of the bacteria may introduce errors in measurements. A sphere is required because the projected area of a sphere is the same for all orientations. Fortunately, the microspheres are uniformly sized (1.5% maximum standard deviation in diameter). However, intensity measurement per cell, using bioluminescence, can be accurately used for bacteria.

Although the CIA method excludes all microspheres not associated with a macrophage, the epi-fluorescence light microscope cannot aid the determination whether microspheres are inside or attached to the outside of a macrophage due to the limitation in depth of the in-focus optical plane. However, the number of microspheres on the outside of the cells was minimized by vigorously washing the cultures after phagocytosis, and inhibition of phagocytosis by cytochalasin B or low temperature (4° C.) treatments showed very few microspheres adhered to the cells (less than one microsphere per cell remained after washing). Nonetheless, rarely an excessive number of microspheres remained after washing and these cultures were not analyzed. "Background" microspheres is defined as greater than 50 individual non-phagocytized microspheres per 1 mm$^2$, and/or microsphere aggregates having an area equal to or greater than a cell.

Other sources of error are the type and sensitivity of the video camera and the mercury arc epi-illumination wattage used. When a low light SIT camera is used, it must be properly adjusted to prevent image bloom of microspheres that increases the area of the individual and/or touching microspheres. Image bloom of microspheres is also caused by a higher than 50 watt mercury arc epiillumination.

Confocal scanning fluorescence microscopy (CSFM), a new light microscope method, provides significantly higher resolution images of microspheres in phagocytes than conventional epi-fluorescence light microscopy due primarily to the exclusion of out-of-focus light, the major limitation in epi-illumination fluorescence microscopy (Hook, GR & Odeyale, CO. J. Leukocyte Biol., 45,277, 1989. Theoretically, using a CSFM as the imaging system for the CIA would provide more accurate phagocytosis data. CSFM can be used to optically section through individual macrophages to determine the three dimensional distribution of microspheres within the cells. Knowing the three-dimensional distribution would eliminate the artifact caused by over laying microspheres discussed above. In addition, combining CSFM with differential interference contrast (DIC) microscopy, microspheres attached to the outside of cells can be resolved from those inside the cells. CSFM would be particularly useful for phagocytosis analysis in cell aggregates. However, due to a significant decrease in the number of cells that could be analyzed because high magnification optical sections are needed, more time, storage space, and computer intensive processing would be required.

Since detailed quantitative morphological data of macrophages attached to substrate is needed to correlate function and structure, in the future, this method will be used with a confocal scanning fluorescence microscope. Nonetheless, CIA will be useful for screening the effects of chemicals on macrophage morphology, phagocytosis, and cell sub-classifications.

Obviously, many modifications and variations of the present invention are possible in light of the above teachings. It is therefore to be understood that, within the scope of the appended claims, the invention may be practiced otherwise than as specifically described.

What is claimed is:

1. A system for quantifying objects comprising:
an imaging means for forming at least two types of images;
a sample mount for mounting a sample containing target cells in said imaging means wherein the target is a relatively large object capable of engulfing smaller enclosed objects;
a first light source mounted on said imaging means for projecting a first beam of light on said sample and forming a contrast image as a first image;
a second light source mounted on said imaging means for projecting a second beam of light on said sample and forming a second image having a different grey value than said first image;
recording means for recording said first and second images;
digitizing means for digitizing said first and second images to form digitized first and second images;
filtering means to filter said first digitized image to form a filtered image;
segmenting means to convert the filtered image and the second digitized image to form first and second binary images;
means for inverting said second binary image to form an inverted binary image; computing means for adding the first binary image and the inverted binary image to form a composite image and determining the number of engulfed objects per target cell using the following formula $$GV = ((0*M) + (255*C))/AR$$

wherein GV is the grey value, AR is the total area of both larger objects and smaller enclosed objects, M is the weighted average of the smaller enclosed objects area and C is the larger object area.

2. The system of claim 1 wherein the larger object is a cell and the smaller object is a microsphere.

3. A method of quantifying objects comprising:
providing a sample containing target cells wherein the target cell is a relatively large object capable of engulfing smaller enclosed objects and smaller potentially enclosed objects;

viewing the sample through an optical system imaging means capable of forming at least two types of images;

projecting a beam of light from a first light source on the sample to form a contrast image as a first image;

projecting a second beam of light on the sample from a second light source to form a second image having a different grey value than said first image;

recording the first and second images;

digitizing the first and second images to form digitized first and second images;

filtering the first digitized image to form a filtered image;

segmenting the filtered image and the second digitized image to form first and second binary images;

inverting said second binary image to form an inverted binary image; adding the first binary image and the inverted binary image to form a composite image; and determining the number of engulfed objects per target cell in the composite image using the following formula $$GV = ((0*M) + (255*C))/AR$$

wherein GV is the grey value, AR is the total area of both cells and engulfed objects, M is the weighted average of the engulfed object area and C is the cell area.

4. The method of claim 3 wherein the composite image is superimposed on the second image to form a superimposed image for determining the number of engulfed objects.

5. A method according to claim 3 wherein the quantitative determination comprises the steps of:

selecting random fields of cells using image forming system;

sequentially acquiring target cells in an image field;

and without moving the sample, acquiring an image of enclosed fluorescent objects;

selecting the cells within the bright or phase contrast field by grey level discrimination and transforming this image into a binary image, discriminating the fluorescent object images from the background and inverting the image formed to black so that the fluorescent objects can be differentiated from the cell, utilizing the discriminated and inverted image field of the enclosed objects as a mask or reference image, and calculating the number of microspheres in each cell by dividing the total fluorescent object area in each cell by the area of a single fluorescent object.

6. A method as in claim 3 wherein said enclosed objects in a larger object is indicative of endocytosis or any form of enclosure.

7. A method as in claim 3 including producing total area of intensity of said enclosed objects.

8. A method as in claim 7 wherein said total area of intensity is indicative of the extent of endocytosis or any form of enclosure.

9. A method as in claim 3 including obtaining said image in the same or different grey values.

10. A method as in claim 3 including the step of:
a) removing artifacts caused by dirt in the optical system,
b) making selected grey value window completely dark by image scaling,
c) enhancing the first image by ranked median filtration,
d) adding the discriminated images of the enclosed objects to that of the enclosing object,
e) analyzing the enclosed objects and graphically displaying the results of said analysis to indicate enhanced or suppressed phagocytic functions.

11. A method as in claim 5 including analyzing said enclosed and enclosing objects for a phagocytosis parameter termed avidity index defined as the mean number of microspheres associated with cells that have engaged in phagocytosis.

12. A method as in claim 5 including analyzing said enclosed and enclosing objects for a phagocytosis parameter termed phagocytic index defined as the mean number of microspheres ingested per cell.

13. A method as in claim 5 including analyzing said enclosed and enclosing objects for a phagocytosis parameter termed phagocytic activity index defined as the percentage of cells out of the total number viewed which have actually ingested objects.

14. A method as in claim 5 including analyzing said enclosed and enclosing objects for a phagocytosis parameter termed phagocytic capacity defined as the grand sum of the engulfed microspheres by the cells all together.

* * * * *